United States Patent
Kokubun et al.

(10) Patent No.: US 10,810,713 B2
(45) Date of Patent: Oct. 20, 2020

(54) IMAGE PROCESSING DEVICE AND IMAGE PROCESSING METHOD

(71) Applicant: Hitachi, Ltd., Tokyo (JP)

(72) Inventors: Hiroto Kokubun, Tokyo (JP); Fuyuhiko Teramoto, Tokyo (JP)

(73) Assignee: Hitachi, Ltd., Tokyo (JP)

(*) Notice: Subject to any disclaimer, the term of this patent is extended or adjusted under 35 U.S.C. 154(b) by 134 days.

(21) Appl. No.: 15/777,964

(22) PCT Filed: Jan. 27, 2017

(86) PCT No.: PCT/JP2017/002839
§ 371 (c)(1),
(2) Date: May 22, 2018

(87) PCT Pub. No.: WO2017/141660
PCT Pub. Date: Aug. 24, 2017

(65) Prior Publication Data
US 2018/0350045 A1    Dec. 6, 2018

(30) Foreign Application Priority Data

Feb. 16, 2016 (JP) .................. 2016-026770

(51) Int. Cl.
*G06T 5/00* (2006.01)
*G06T 7/11* (2017.01)
(Continued)

(52) U.S. Cl.
CPC ............. *G06T 5/008* (2013.01); *A61B 5/00* (2013.01); *A61B 5/055* (2013.01); *G06T 7/0012* (2013.01);
(Continued)

(58) Field of Classification Search
None
See application file for complete search history.

(56) References Cited

U.S. PATENT DOCUMENTS

| 5,900,732 A | * | 5/1999 | Felmlee | G01R 33/56 |
| | | | | 324/307 |
| 2004/0064038 A1 | * | 4/2004 | Bruder | G06T 5/007 |
| | | | | 600/425 |

(Continued)

FOREIGN PATENT DOCUMENTS

| JP | H0962836 A | * | 3/1997 |
| JP | 2008113850 A | * | 5/2008 |

(Continued)

OTHER PUBLICATIONS

International Search report and Written Opinion for the International Application No. PCT/JP2017/002839, dated Apr. 25, 2017, 1 page.

*Primary Examiner* — Vu Le
*Assistant Examiner* — Tracy Mangialaschi
(74) *Attorney, Agent, or Firm* — Baker Botts L.L.P.

(57) ABSTRACT

To provide an image processing device and an image processing method capable of controlling contrast of a diagnosed part without greatly changing the characteristic of the entire image, and improving the diagnosis efficiency, an image processing device 100 sets a search pixel range and a search region to search for a representative pixel value as reference upon emphasis on the contrast of a diagnostic image as image data of a diagnosis object, calculates the representative pixel value for emphasis processing based on the set search pixel value range and the search region, and generates an emphasized image where the contrast of the entire diagnostic image is emphasized with the representative pixel value as reference. Further, the image processing device 100 calculates an emphasis region as a region where the contrast is emphasized from differential information between the diagnostic image and the emphasized image, (Continued)

and generates a partially emphasized image as an image where the contrast of the emphasis region is emphasized.

18 Claims, 16 Drawing Sheets

(51) Int. Cl.
  *G06T 7/00* (2017.01)
  *A61B 5/00* (2006.01)
  *A61B 5/055* (2006.01)
  *G16H 30/40* (2018.01)

(52) U.S. Cl.
  CPC ............... *G06T 7/11* (2017.01); *G16H 30/40* (2018.01); *G06T 2207/10081* (2013.01); *G06T 2207/20021* (2013.01)

(56) References Cited

U.S. PATENT DOCUMENTS

| | | | |
|---|---|---|---|
| 2006/0050938 A1* | 3/2006 | Raupach | G06T 5/009 382/127 |
| 2010/0014729 A1* | 1/2010 | Choi | G06T 5/50 382/131 |
| 2012/0201344 A1* | 8/2012 | Feuerlein | A61B 6/032 378/4 |
| 2012/0257808 A1 | 10/2012 | Spitzer et al. | |
| 2012/0269413 A1* | 10/2012 | Hautvast | G06T 11/206 382/128 |

FOREIGN PATENT DOCUMENTS

| | | |
|---|---|---|
| JP | 2008113850 A | 5/2008 |
| JP | 4707471 B2 | 6/2011 |

* cited by examiner

41 SEARCH PIXEL VALUE RANGE DATA

| INSPECTED PART | SEARCH PIXEL VALUE RANGE | |
|---|---|---|
| | LOWER LIMIT VALUE | UPPER LIMIT VALUE |
| HEAD | 30 | 40 |
| BREAST | −700 | −500 |
| ABDOMEN | 30 | 50 |
| ... | ... | ... |

56 CONDITION TABLE

| SELECT | EMPHASIS OBJECT | SEARCH PIXEL VALUE RANGE | |
|---|---|---|---|
| | | LOWER LIMIT VALUE | UPPER LIMIT VALUE |
| ✓ | OBJECT A | 30 | 40 |
| ✓ | OBJECT B | 45 | 55 |
| | OBJECT C | 5 | 15 |
| ... | ... | ... | ... |

(a)

(b)

IMAGE PROCESSING DEVICE AND IMAGE PROCESSING METHOD

CROSS-REFERENCE TO RELATED APPLICATIONS

This application is a national phase claiming the benefit of and priority to International Patent Application No. PCT/JP2017/002839, entitled IMAGE PROCESSING "DEVICE AND IMAGE PROCESSING METHOD", filed Jan. 27, 2017, which claims priority to Japanese Patent Application No. 2016-026770, filed Feb. 16, 2016, which are hereby incorporated by reference in their entireties.

TECHNICAL FIELD

The present invention relates to an image processing device and an image processing method, and more particularly, to image processing to efficiently diagnose a low-contrast part.

BACKGROUND ART

In diagnosis using a medical image, a part having small density difference may become a diagnosis object in some cases. In such case, it is not possible to correctly grasp the shape of a diagnosis object organ or it is not possible to discriminate a lesion to be detected. Further, in some cases, it is difficult to perform further correct diagnosis due to occurrence of noise or false image (artifact) depending on image generation condition. In such case, nonlinear grayscale conversion (e.g. gamma correction) may be performed so as to increase density contrast of a tissue as a diagnosis object. With this processing, it is possible to increase the density contrast of the diagnosis object tissue; however, when a pixel having an equivalent density to the diagnosis object tissue exists around the object, the pixel value of other tissue than the diagnosis object also varies. It hinders efficient diagnosis.

Patent Literature 1 describes a technique (adaptive filter processing) of analyzing the structure (pixel value distribution) of a diagnosis object by local region of an image, and dynamically selecting the content of image processing.

CITATION LIST

Patent Literature

PTL 1: Japanese Patent No. 4707471

SUMMARY OF INVENTION

Technical Problem

However, in the method in the Patent Literature 1, the structure of the diagnosis object must be clear. In a low contrast region, it is difficult to apply the processing of analyzing the structure of the diagnosis object and selecting processing content as described above.

The present invention has been made in view of the above problem, and has an object to provide an image processing device and an image processing method capable of controlling the contrast of a diagnosed part without greatly changing the characteristic of the entire image and improving diagnosis efficiency.

Solution to Problem

To achieve the above-described object, the present invention provides: an image processing device including: a diagnostic image input unit that inputs a diagnostic image as image data of a diagnosis object; a search pixel value range setting unit that sets a search pixel value range as a pixel value range to search for a representative pixel value as reference upon emphasis on contrast of the diagnostic image; a search region setting unit that sets a search region as a region to search for the representative pixel value; a representative pixel value calculation unit that calculates the representative pixel value based on the set search pixel value range and the search region; an emphasized image generation unit that generates an emphasized image as an image where the contrast of the entire diagnostic image is emphasized with the calculated representative pixel value as reference; an emphasis region calculation unit that calculates an emphasis region as a region where the contrast is emphasized from the diagnostic image and the emphasized image; and a partially emphasized image generation unit that generates a partially emphasized image as an image where the contrast of the emphasis region is emphasized.

Further, the present invention provides: an image processing method using a computer, including: a step of inputting a diagnostic image as image data of a diagnosis object; a step of setting a search pixel value range as a pixel value range to search for a representative pixel value as reference upon emphasis on contrast of the diagnostic image; a step of setting a search region as a region to search for the representative pixel value; a step of calculating the representative pixel value based on the set search pixel value range and the search region; a step of generating an emphasized image as an image where the contrast of the entire diagnostic image is emphasized with the calculated representative pixel value as reference; a step of calculating an emphasis region as a region where the contrast is emphasized from the diagnostic image and the emphasized image; and a step of generating a partially emphasized image as an image where the contrast of the emphasis region is emphasized.

Advantageous Effects of Invention

With the present invention, it is possible to provide an image processing device and an image processing method capable of controlling the contrast of a diagnosed part without greatly changing the characteristic of the entire image and improving diagnosis efficiency.

DESCRIPTION OF EMBODIMENTS

Hereinbelow, embodiments of the present invention will be described in detail based on the drawings.

First Embodiment

First, the configuration of an image processing system 1 to which an image processing device 100 according to the present invention is applied will be described with reference to FIG. 1.

Figure 1:
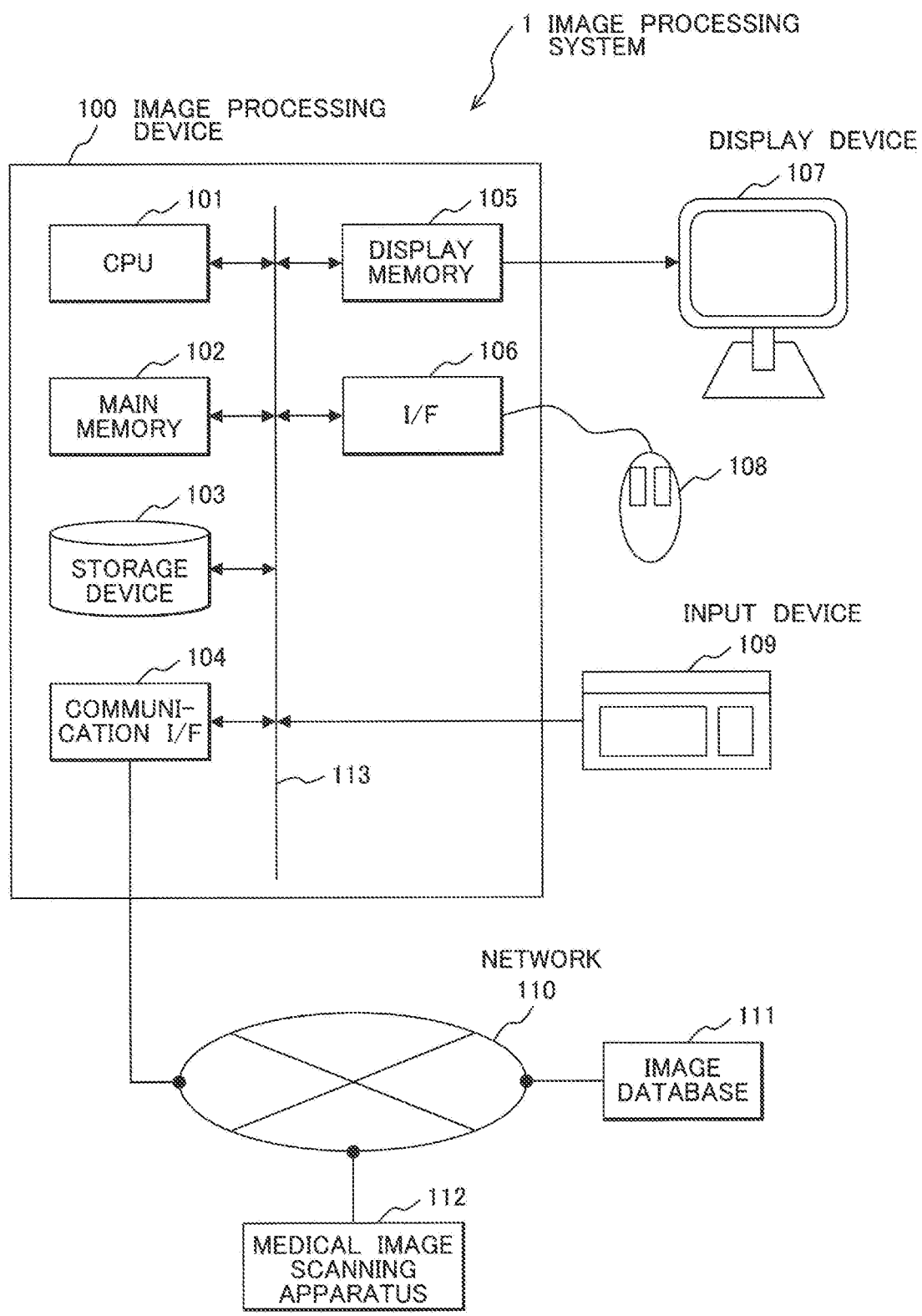
FIG. 1 is a diagram showing the entire configuration of an image processing device 100.

As shown in FIG. 1, the image processing system 1 has the image processing device 100, an image database 111 connected to the image processing device 100 via a network 110, and a medical image scanning apparatus 112.

The image processing device 100 is a computer to perform processing including image generation and image analysis. As shown in FIG. 1, the image processing device 100 has a CPU (Central Processing Unit) 101, a main memory 102, a storage device 103, a communication interface (communication I/F) 104, a display memory 105, and an interface (I/F) 106 with respect to external devices such as a display device 107, an input device 109, and a mouse 108. The respective elements are connected via a bus 113.

The CPU 101 reads a program stored in the main memory 102, the storage device 103 or the like to a work memory area on a RAM of the main memory 102 and performs the program. The CPU drive-controls the respective elements connected via the bus 113, to realize various processing performed with the image processing device 100.

The CPU 101 of the image processing device 100 generates a partially emphasized image, in which the contrast of a diagnosed part is emphasized, and initial pixel value in a not-diagnosed part is maintained. The details of the partially emphasized image generation processing (see FIG. 4) will be described later.

The main memory 102 has a ROM (Read Only Memory), the RAM (Random Access Memory), and the like. The ROM permanently holds a boot program, BIOS and the like for the computer, data, and the like. Further, the RAM temporarily holds a program, data and the like loaded from the ROM, the storage device 103 and the like. The RAM has a work area used with the CPU 101 for execution of various processing.

The storage device 103 is a storage device for data reading/writing with respect to an HDD (Hard Disk Drive) or other recording medium. The programs performed with the CPU 101, data necessary for execution of the programs, the OS (Operating System) and the like are stored in the storage device 103. Regarding the programs, a control program corresponding to the OS and application programs are stored. The respective program codes are read with the CPU 101 in accordance with necessity and transferred onto the RAM of the main memory 102, and performed as various means.

The communication I/F 104 has a communication control device, a communication port and the like. The communication I/F 104 functions as an interface for communication between the image processing device 100 and the network 110. Further, the communication I/F 104 performs communication control, with respect to the image database 111, another computer, or the medical image scanning apparatus 112 such as an X-ray CT apparatus, an MRI device or the like via the network 110.

The I/F 106 is a port for connection with peripheral devices. The I/F 106 performs data transmission/reception with respect to the peripheral devices. For example, it may be configured such that a pointing device such as the mouse 108 or a stylus pen is connected via the I/F 106.

The display memory 105 is a buffer for temporary storage of display data inputted from the CPU 101. The stored display data is outputted at predetermined timing to the display device 107.

The display device 107 has a display device such as a liquid crystal panel or a CRT monitor, and a logic circuit to perform display processing in cooperation with the display device. The display device 107 is connected via the display memory 105 to the CPU 101. The display device 107 displays the display data stored in the display memory 105 under the control of the CPU 101.

The input device 109 is an input device which is e.g. a keyboard. The input device 109 outputs various instructions and information inputted by an operator to the CPU 101. The operator interactively operates the image processing device 100 using the external devices such as the display device 107, the input device 109, and the mouse 108.

The network 110 includes various communication networks such as a LAN (Local Area Network), a WAN (Wide Area Network) and the Internet. The network 110 mediates communication connection between the image database 111, a server and other information devices, and the image processing device 100.

The image database 111 stores image data obtained with the medical image scanning apparatus 112 and holds the data. In the image processing system 1 shown in FIG. 1, the image database 111 is connected via the network 110 to the image processing device 100. It may be configured such that the image database 111 is provided in, e.g. the storage device 103, in the image processing device 100.

Next, the functional configuration of the image processing device 100 will be described with reference to FIG. 2.

Figure 2:
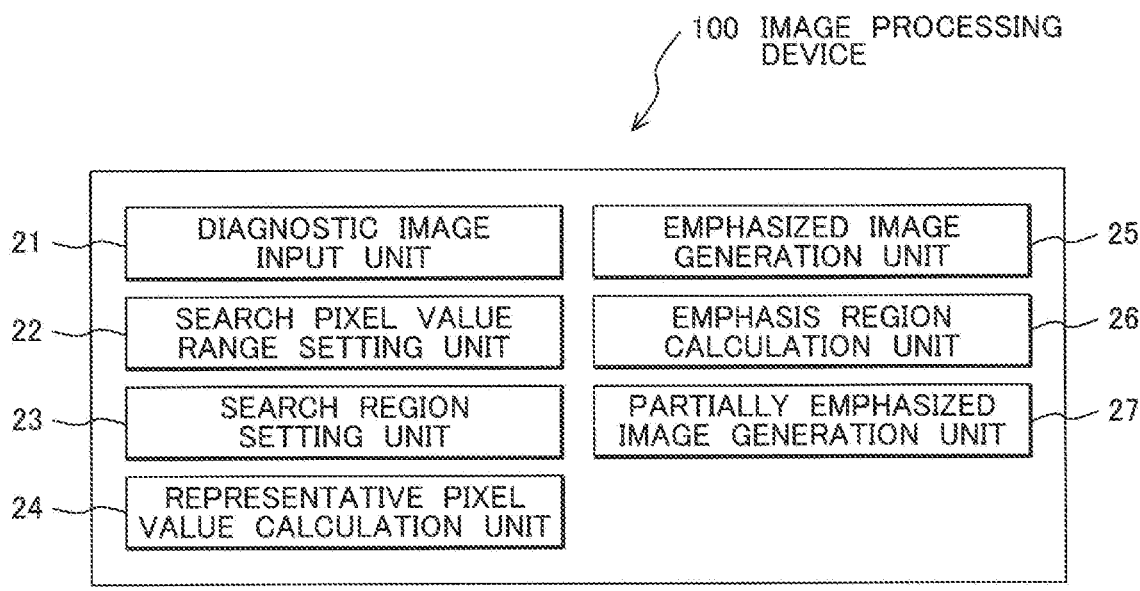
FIG. 2 is a block diagram showing the functional configuration of the image processing device 100.

As shown in FIG. 2, the image processing device 100 has a diagnostic image input unit 21, a search pixel value range setting unit 22, a search region setting unit 23, a representative pixel value calculation unit 24, an emphasized image generation unit 25, an emphasis region calculation unit 26, and a partially emphasized image generation unit 27.

The diagnostic image input unit 21 reads image data as a diagnosis object from the storage device 103, the medical image scanning apparatus 112 or the image database 111, and holds the data in the main memory 102. The image data indicates plural tomographic images obtained by photographing a subject by using an X-ray CT apparatus, an MR apparatus or the like. Hereinbelow, a case where the input image is a CT image will be described. Further, the input image is referred to as a diagnostic image.

The search pixel value range setting unit 22 sets a pixel value range to search for a representative pixel value on the diagnostic image (hereinbelow, referred to as a "search pixel value range") to calculate a representative pixel value as reference upon generation of an emphasized image to be described later. The search pixel value range is set as a combination of a minimum value and a maximum value. An appropriate search pixel value range may be previously registered in the storage device 103, or the operator may input an arbitrary search pixel value range using the input device 109. It is desirable that as the search pixel value range, an appropriate pixel value range is set in accordance with part as a diagnosis object.

The search region setting unit 23 sets a region to search for the representative pixel value of the diagnostic image, on the diagnostic image. The shape and the size of the search region may be previously registered in the storage device 103 of the image processing device 100, or the operator may input an arbitrary shape using the input device 109. It is desirable that as the search region, a region having appropriate shape and size is set in accordance with part as a diagnosis object.

The representative pixel value calculation unit 24 calculates the representative pixel value from the diagnostic image based on the set search pixel value range and the search region. The representative pixel value calculation unit 24 first extracts pixels which stand within the search region set with the search region setting unit 23 and which have pixel values included in the pixel value range set with the search pixel value range setting unit 22. Then the representative pixel value calculation unit 24 calculates a pixel value representing the search region (representative pixel value) from the pixel values of the extracted plural pixels. There are various methods for calculating a representative pixel value. In the present embodiment, as an example, a mean value of the pixel values of all the extracted pixels is obtained as a representative pixel value.

Figure 3:
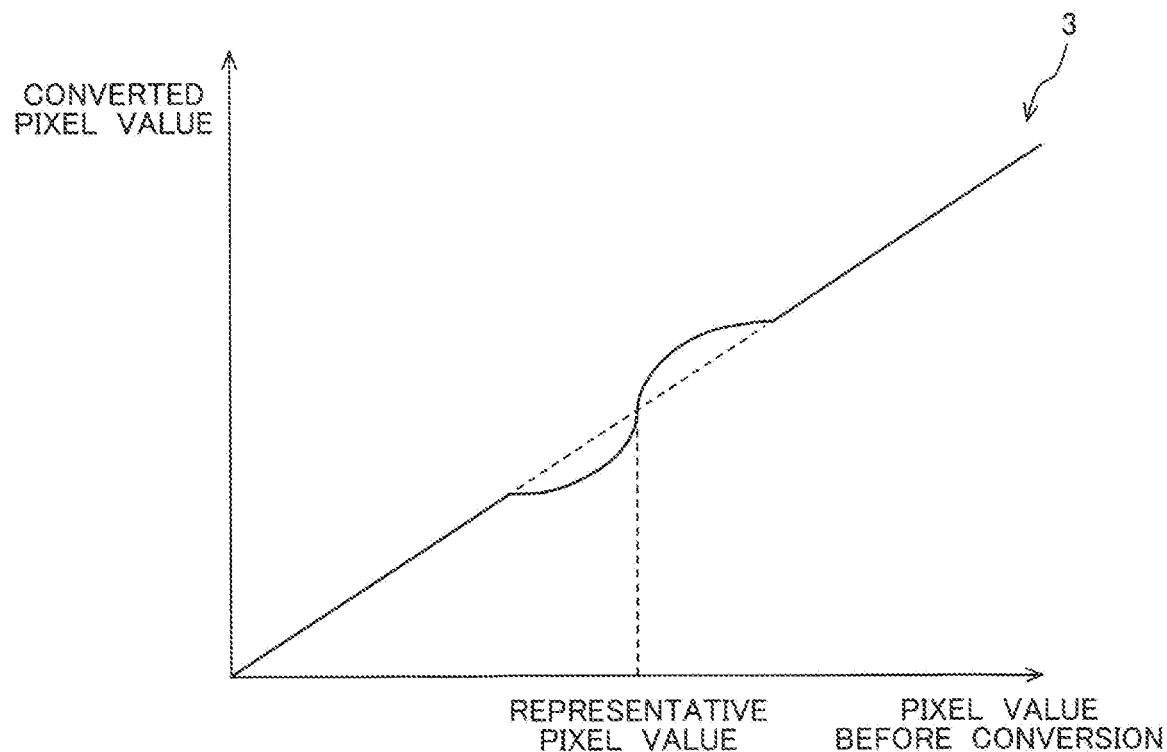
FIG. 3 is a diagram showing an example of nonlinear grayscale conversion with a representative pixel value as reference.

The emphasized image generation unit 25 generates an emphasized image as an image where the contrast of the diagnostic image is emphasized, with the representative pixel value calculated with the representative pixel value calculation unit 24 as reference. For example, the contrast front and behind the representative pixel value is emphasized by grayscale conversion using a nonlinear function (nonlinear grayscale conversion). FIG. 3 shows an example of the nonlinear grayscale conversion. As shown in FIG. 3, grayscale conversion is performed by using a function 3 so as to increase the pixel value difference front and behind the representative pixel value. The emphasized image generation unit 25 generates the emphasized image by performing this grayscale conversion on all the pixels of the diagnostic image inputted with the diagnostic image input unit 21.

The emphasis region calculation unit 26 calculates an emphasis region, as a region where the contrast is emphasized, based on the diagnostic image and the emphasized image. The emphasis region calculation unit 26 obtains the difference between the diagnostic image and the emphasized image, then calculates the emphasis region based on the magnitude of variation of the difference value. The particular emphasis region calculation method will be described later.

The partially emphasized image generation unit 27 generates an image where the contrast of the emphasis region calculated with the emphasis region calculation unit 26 is emphasized (partially emphasized image). The particular partially emphasized image generation method will be described later.

Next, the flow of partially emphasized image generation processing performed with the image processing device 100 according to the first embodiment will be described with reference to the flowchart of FIG. 4 and FIG. 5.

The CPU 101 (diagnostic image input unit 21) of the image processing device 100 inputs a diagnostic image 31 as a processing object from the storage device 103 or the image database 111 connected via the communication I/F 104 (step S101).

Next, to calculate a representative pixel value as reference of emphasized image generation processing at step S105, the CPU 101 (search pixel value range setting unit 22) first sets a pixel value range as a search object (hereinbelow, search pixel value range) (step S102). As the search pixel value range, a value previously registered as a combination of minimum and maximum pixel values in the storage device 103 of the image processing device 100 is used. Otherwise, an arbitrary search pixel value range inputted by the operator by using the input device 109 or the like may be used. For example, regarding a head, the search pixel value range is set as "30 to 40"; and regarding a breast, the search pixel value range is set as "−700 to −500".

Next, to calculate the representative pixel value as reference of emphasized image generation processing to be described later, the CPU 101 (search region setting unit 23) sets a search region in an appropriate shape on the diagnostic image (step S103). The shape and size of the search region may be previously registered in the storage device 103 of the image processing device 100. Otherwise, the operator may input by using the input device 109 or the like. Further, the search region may be set by image, or may be set in plural images continuous in a body axis direction.

Next, the CPU 101 (representative pixel value calculation unit 24) extracts pixels having pixel values included in the search pixel value range set at step S102 from the search region set at step S103 (step S104). Then the CPU 101 calculates a pixel value representing the search region (representative pixel value) from the extracted plural pixels. There are various methods for calculating a representative pixel value. In the present embodiment, as an example, a mean value of the pixel values of all the extracted pixels is obtained as a representative pixel value.

The CPU 101 (emphasized image generation unit 25) generates an emphasized image as an image where the contrast is emphasized with the representative pixel value calculated at step S104 as a reference value (step S105). In the present embodiment, for example, as shown in FIG. 3, grayscale conversion is performed by using the nonlinear function 3 to increase the pixel value difference front and behind the representative pixel value. With this conversion, the contrast front and behind the representative pixel value is emphasized. The CPU 101 performs the grayscale conversion on all the pixels of the diagnostic image inputted at step S101, to generate the emphasized image where the contrast of the entire image is emphasized.

The CPU 101 (emphasis region calculation unit 26) calculates an emphasis region to which contrast emphasis processing is finally applied based on the diagnostic image inputted at step S101 and the emphasized image generated at step S105 (step S106). An example of emphasis region calculation method will be described with reference to FIG. 5.

As shown in FIG. 5(a), the diagnostic image 31 includes a diagnosed part 31a where the contrast is low and a not-diagnosed part 31 having pixel values approximately equivalent to those of the diagnosed part 31a. The present invention has an object to generate a "partially emphasized image" where the pixel values of the not-diagnosed part 31b do not vary while emphasize the contrast in the diagnosed part 31a. FIG. 5(b) shows a conceptual diagram of an emphasized image 33 obtained by performing the emphasis processing at step S105 on the diagnostic image 31 in FIG. 5(a). In comparison with the diagnostic image 31 in FIG. 5(a), in the emphasized image 33 shown in FIG. 5(b), the pixel value difference (contrast) in the diagnosed part 31a is emphasized. Further, as the pixel values in a part of the diagnosed part 31a and those in the not-diagnosed part 31b are approximately equivalent, as a result of emphasis processing, the pixel values in the not-diagnosed part 31b also vary.

To calculate the emphasis region as a finally emphasized region, the CPU 101 first generates a differential image 35 obtained by subtracting the diagnostic image 31 from the emphasized image 33. Then as shown in FIG. 5(c), the differential image 35 corresponding to the effect of the emphasis processing performed at step S105 is obtained.

In the differential image 35, since the emphasis processing is performed, with the representative pixel value calculated at step S104 as reference, in a region corresponding to the diagnosed part 31a, positive and negative pixel values are intermingled, and the difference value variation (change) is large. On the other hand, in a region corresponding to the not-diagnosed part 31b, since the pixel values are one-sided to positive or negative, the difference value variation (change) is small. By utilizing this characteristic, the CPU 101 determines that a region where the difference value variation (change) is large as an emphasis region 37. The emphasis region 37 is calculated as shown in FIG. 5(d).

The CPU 101 (partially emphasized image generation unit 27) combines the diagnostic image 31 with the emphasized image 33 based on the emphasis region 37 calculated at step S106, and generates a partially emphasized image where the contrast of the diagnosed part 31a is emphasized (step S107).

The CPU 101 displays the generated partially emphasized image on the display device 107 (step S108). The operator performs image diagnosis while refers to the displayed partially emphasized image.

The CPU 101 repeatedly performs the processing at above-described steps S101 to step S108 in the image range (respective images in the body axis direction) in the diagnosed part 31a. Since the representative pixel value at step S104 is calculated with respect to the respective images, in the partially emphasized image generated at step S107, the pixel values and tissue shapes in the respective regions are reflected.

The emphasis region calculation processing at step S106 will be further described.

Figure 6:
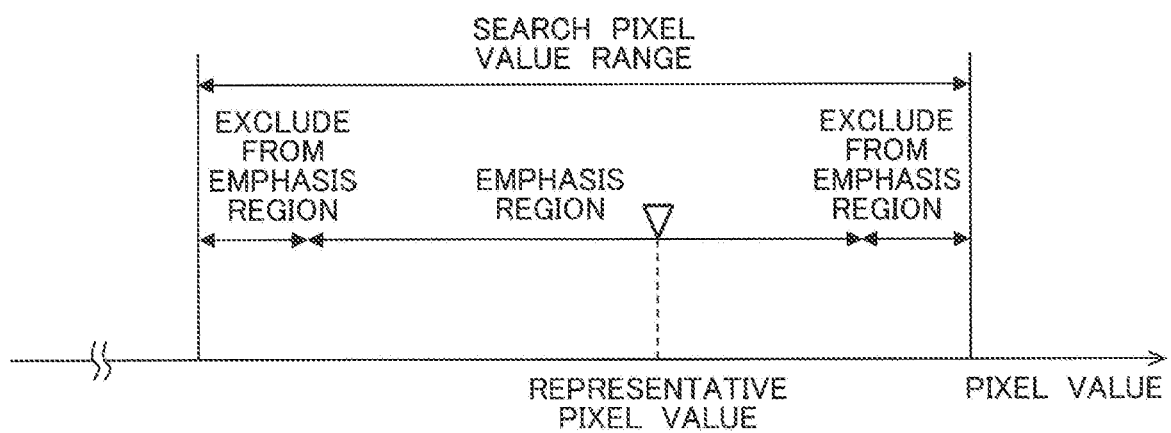
FIG. 6 is a diagram explaining an example of providing an emphasis exclusion range at both ends of a search pixel value range.

The CPU 101 may calculate the emphasis region based on the relationship between the search pixel value range set at step S102 and the representative pixel value calculated at step S104. FIG. 6 shows the concept of the calculation.

As the representative pixel value is calculated based on the pixel values within the search pixel value range, it exists in the search pixel range. However, the pixel values may be one-sided in accordance with search region setting at step S103, and in some cases, the representative pixel value is close to the value at an end of the search pixel value range. In such situation, there is a region where the number of pixels as diagnosis objects existing within the search pixel value range is small. In view of this problem, it may be configured such that an emphasis exclusion range is provided in the vicinity of the end of the search pixel value range, and when a representative pixel value in a region arbitrarily set in the search region exists in the emphasis exclusion range, the region is excluded from the emphasis region. With this configuration, it is possible to efficiently obtain an emphasis region.

Figure 7:
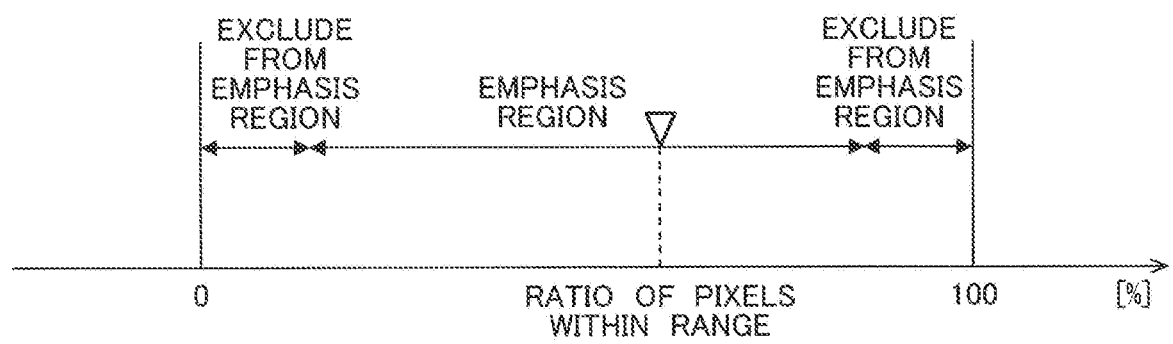
FIG. 7 is a diagram explaining an example of excluding a search region from an emphasis region based on the ratio of pixels within the search pixel value range included in the search region.

Further, in the emphasis region calculation processing at step S106, the CPU 101 may calculate the emphasis region from the ratio of search pixel values in the search region. FIG. 7 shows the concept of the calculation.

It is expected that pixels within the search pixel value range are included in the search region. For example, when the scope of the search region is small and almost all the pixels in the region are included in the search pixel range, all the pixels in the search region are emphasized, and the image becomes unnatural in some cases. On the other hand, when the scope of the search region is large and the number of pixels within the search pixel value range existing in the region is small, only a particular region is emphasized and the image becomes unnatural in some cases. In view of these problems, the ratio of pixels within the search pixel value range in an arbitrary region in the search region is obtained, and when the ratio is equal to or higher than an arbitrary value, or equal to or lower than the value, the region is excluded from the emphasis region. With this configuration, it is possible to efficiently obtain an emphasis region.

Further, it may be configured such that in the emphasis region calculation processing at step S106, the CPU 101 divides the diagnostic image 31 into e.g. blocks, and determines by divided region whether or not it is an emphasis region. Hereinbelow, each divided region will be referred to as an "evaluation block".

Figure 8:
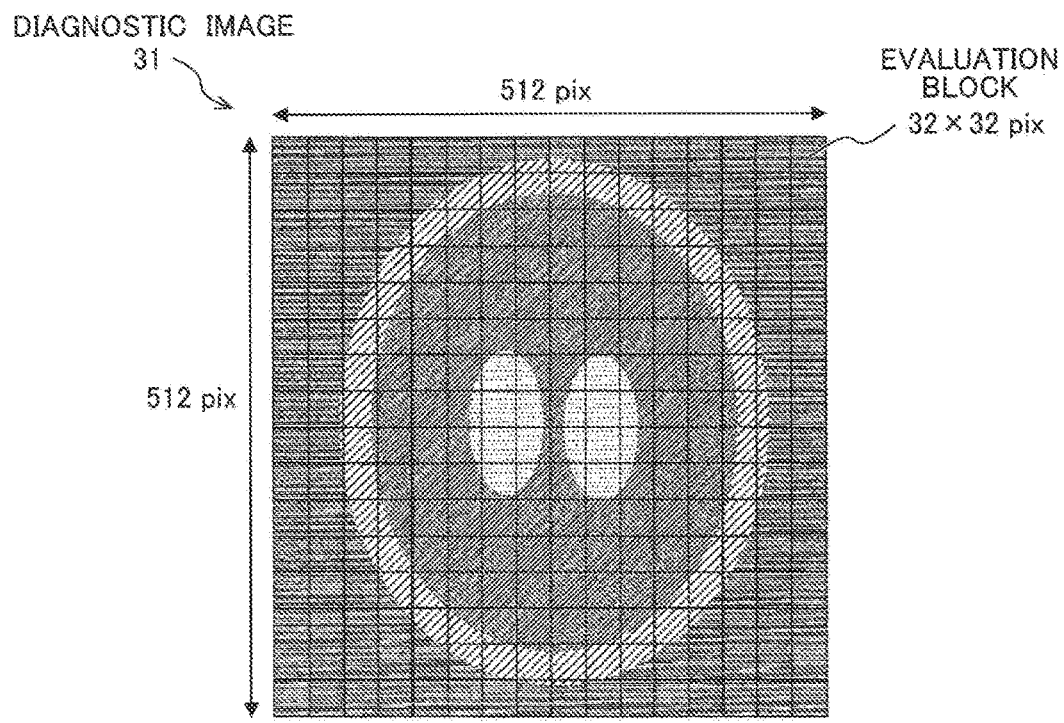
FIG. 8 is a diagram showing an example of an evaluation block set in a diagnostic image 31.

For example, as shown in FIG. 8, when the diagnostic image 31 has 512×512 pixels, the image is divided into 16×16 blocks as evaluation blocks each having 32×32 pixels. The emphasis region determination as described above (determination in FIG. 6 and FIG. 7 as to whether or not it belongs to the emphasis exclusion range) is performed by each of these evaluation blocks, to calculate an emphasis region.

Figure 9:
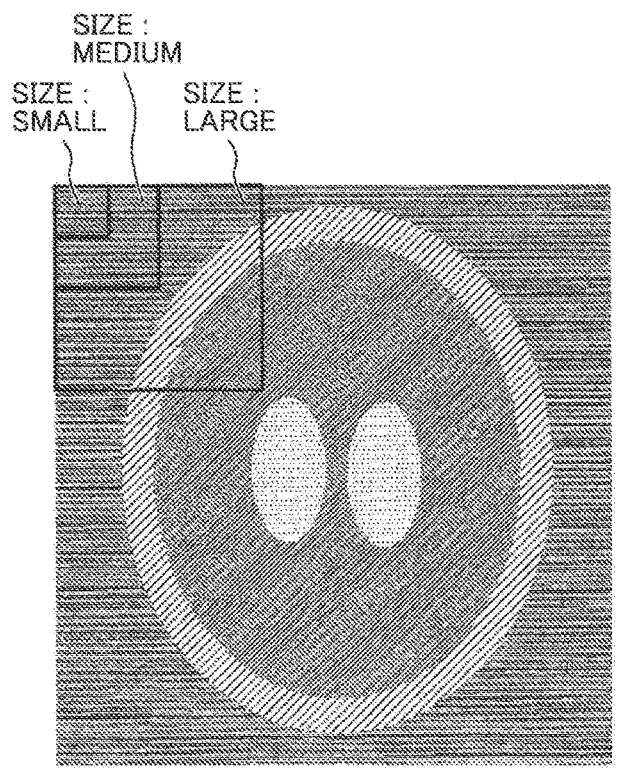
FIG. 9 is a diagram explaining the size of the evaluation block.

Note that it is desirable that as the size of evaluation block for emphasis region determination, an optimum size is set by a part as a diagnosis object. As shown in FIG. 9, when the size of evaluation block for the emphasis region determination is small, although it is possible to evaluate a peripheral pixel region of the diagnosed part in detail, it is difficult to determine a widely distributed tissue. On the other hand, when the size is large, although it is possible to determine a widely distributed tissue, it is difficult to evaluate a detailed part. In view of these problems, it is desirable to determine an appropriate evaluation block size in consideration of shape and size of diagnosed part and perform the emphasis region calculation.

When the emphasis region calculation is performed by evaluation block and the partially emphasized image is generated at step S107, in some cases, the original diagnostic image 31 and the contrast-emphasized emphasized image 33 are changed by evaluation block, and the partially emphasized image becomes unnatural. Accordingly, it is desirable that the determination result by evaluation block is expanded to the pixel size of the diagnostic image 31, and is used as a weight map 38 for smoothly mixing the diagnostic image and the emphasized image.

Figure 10:
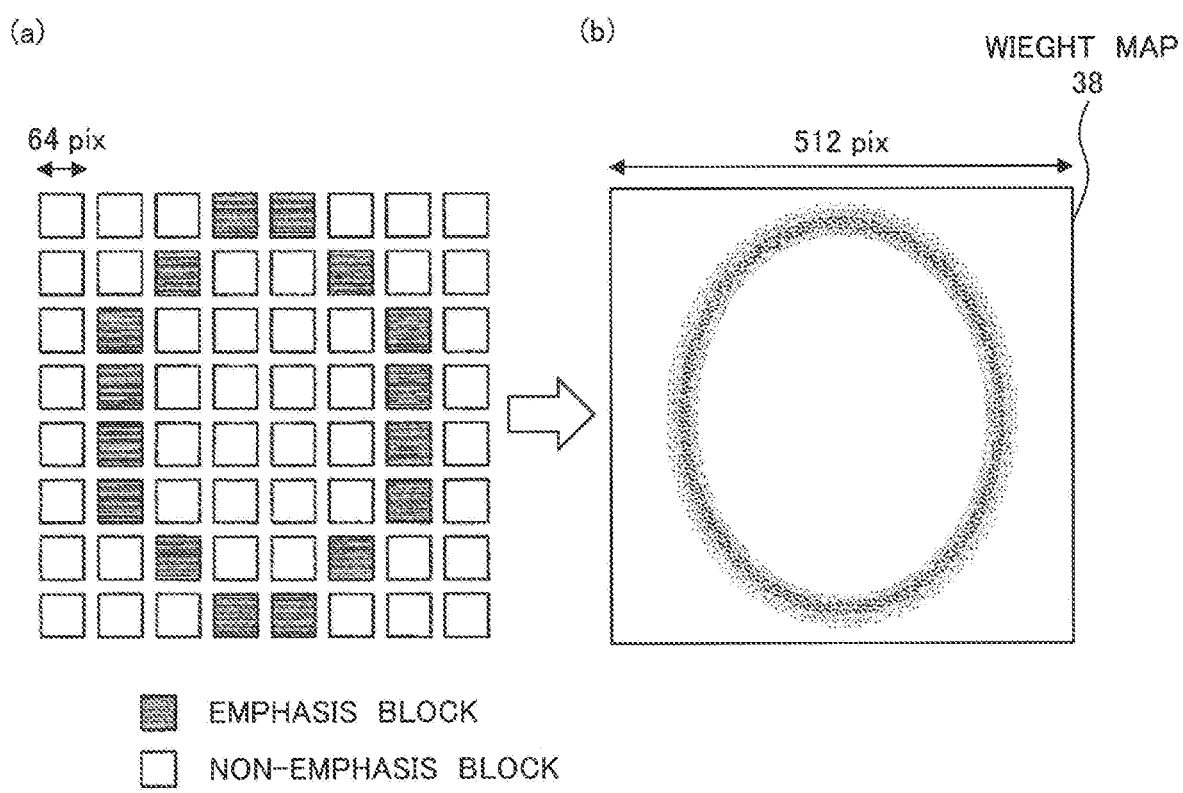
FIG. 10 is a diagram explaining a weight map 38.

FIG. 10 shows an example of generation of the weight map 38. As shown in FIG. 10(a), the size of the evaluation block is 64×64 pixels, and the size of the diagnostic image 31, 512×512 pixels. First, by evaluation block, a weight value "1.0" is assigned to a block which is not an emphasis object, while a weight value "0.0" is assigned to an emphasis object block. Next, by pixel position in the diagnostic image 31, a weight value of an adjacent evaluation block is interpolated and continuous weight values "0.0" to "1.0" are assigned. By execution of the above processing, as shown in FIG. 10(b), the weight map 38 where weight values are respectively assigned to the 512×512 pixels is obtained. In FIG. 10(b), density values of the weight map 38 represent the weight sizes.

Figure 11:
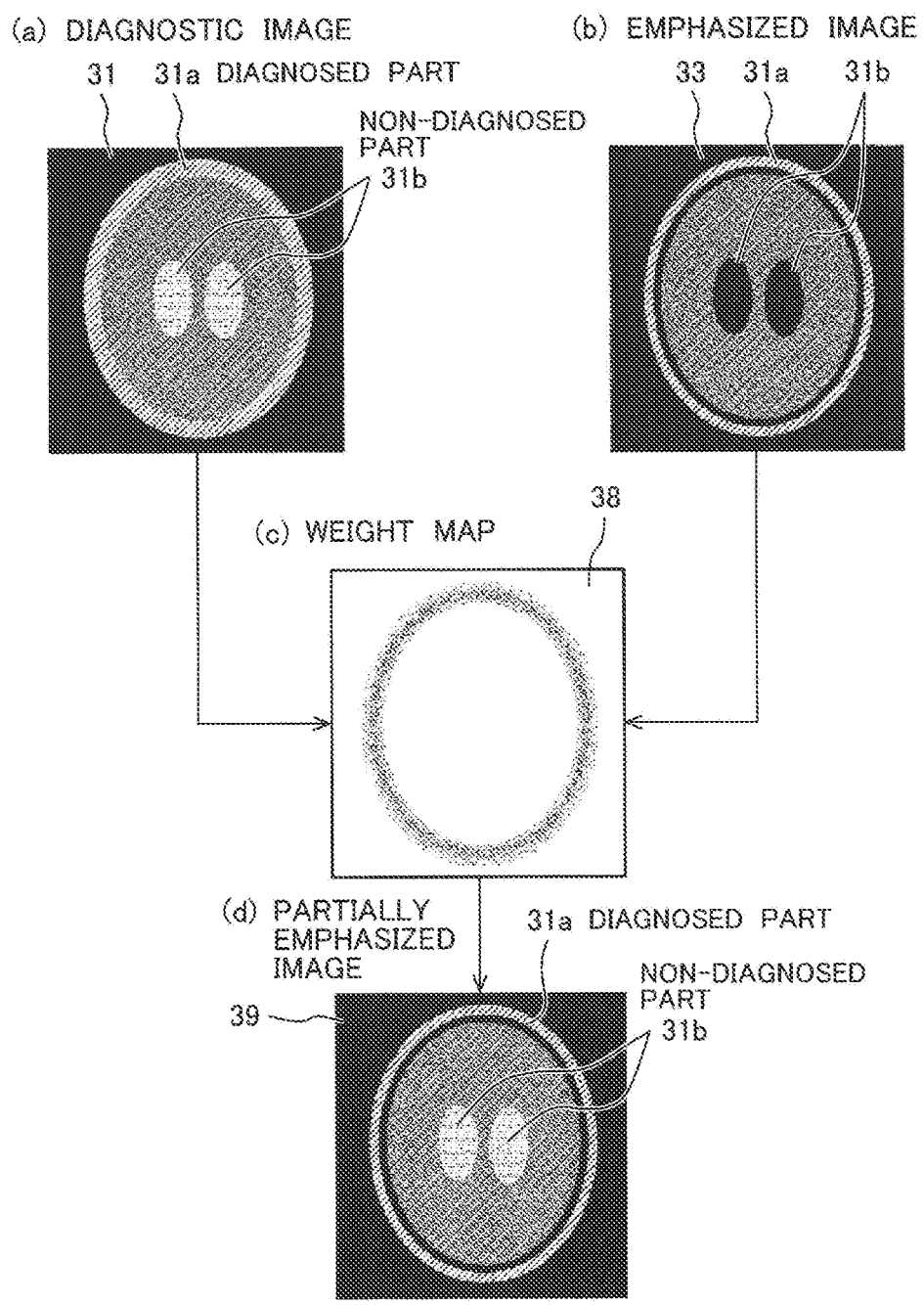
FIG. 11 is a diagram showing an example of generation of a partially emphasized image 39 by using the weight map 38 in FIG. 10.

FIG. 11 shows an example of generation of a partially emphasized image 39 using the weight map 38 in FIG. 10.

As shown in FIG. 11, the CPU 101 mixes the diagnostic image 31 and the emphasized image 33 to generate the partially emphasized image 39. At this time, the CPU 101 refers to a weight value corresponding to the same pixel position from the weight map 38, and performs weighing addition on the diagnostic image 31 and the emphasized image 33. By using the weight map 38, it is possible to generate the natural partially emphasized image 39 where the change between the diagnostic image 31 and the emphasized image 33 is inconspicuous.

Figures 12, 13:
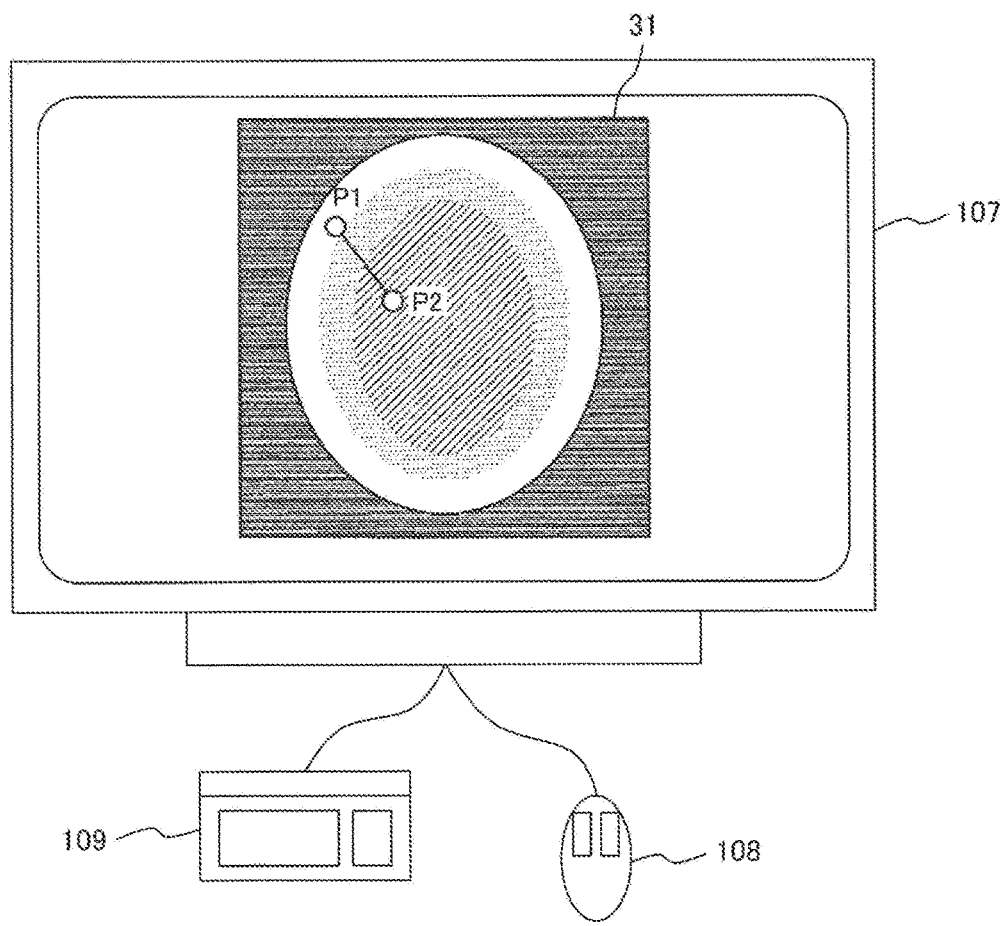
FIG. 12 is a diagram showing an example of search pixel value range data 41 as a data set of an inspected part and the search pixel value range.
FIG. 13 is a diagram showing an example of user interface to set the search pixel value range.

Next, the setting of the search pixel value range at step S102 will be further described. As described above, the optimum search pixel value range differs according to inspected part and tissue. Accordingly, it may be configured such that an optimum search pixel value range is associated to an inspected part, and is held in the storage device 103 of the image processing device 100. FIG. 12 shows an example of search pixel value range data 41 as a data set of inspected part and search pixel value range. In the search pixel value range data 41 shown in FIG. 12, with an inspected part such as head, breast, or abdomen as a key, a search pixel value range (lower limit value and upper limit value) is stored. In the search pixel value range setting processing at step S102, when the operator sets an object inspected part, the CPU 101 obtains a search pixel value range from the search pixel value range data 41 with the set inspected part as a key, and sets the range in the image processing device 100. With this configuration, an optimum search pixel value range is set in accordance with inspected part.

Further, it may be configured such that the operator sets the search pixel value range at step S102 by his/her operation while refers to the diagnostic image 31 displayed on the display device 107. FIG. 13 is a diagram showing an example of the user interface for setting the search pixel value range. As shown in FIG. 13, the CPU 101 of the image processing device 100 displays the diagnostic image 31 on the display device 107. The operator uses the input device 109, the mouse 108 and the like, to specify a part which has low contrast on the displayed diagnostic image 31 to cause difficulty in diagnosis.

The specify operation may be, e.g., as shown in FIG. 13, an operation of specifying a large pixel value point P1 and a small pixel value point P2 in a desired diagnosed part of the diagnostic image 31. The CPU 101 sets the specified point P1 as an upper limit value of the search pixel value range, and the specified point P2, as a lower limit value of the search pixel value range. With this configuration, the user sets the search pixel value range while actually checks the contrast (gradation) on the image. Note that the number of specified points is not limited to two but may be two or more. When two or more points are set, a maximum value and a minimum value among pixel values of the specified plural points (pixels) are set as the search pixel value range.

The search region setting at step S103 will be further described.

Figure 14:
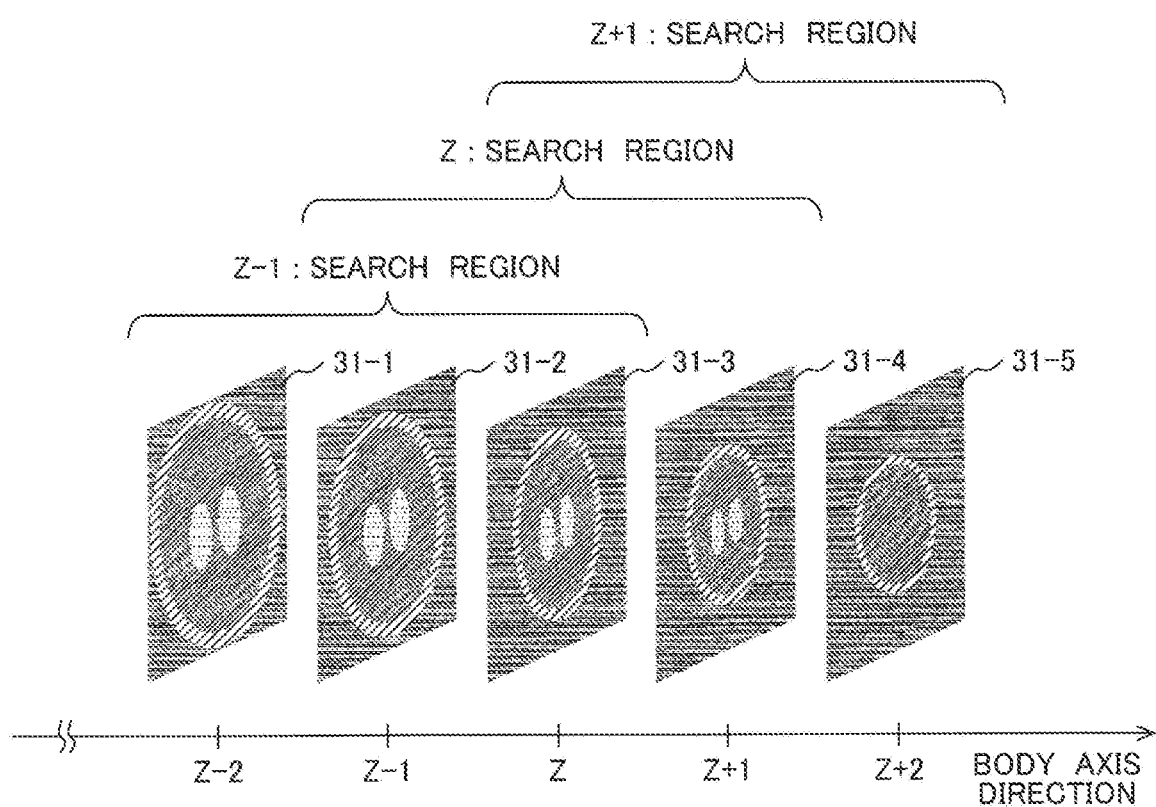
FIG. 14 is a diagram showing an example of setting the search region in plural images continuing in a body axis direction.

Upon search region setting, when a search region is set with respect to a particular image, as a representative pixel value is calculated by each image position (position in the body axis direction), there is a fear that the continuity of the representative pixel values in the body axis direction is impaired. Accordingly, as shown in FIG. 14, it may be configured such that the search region is set in plural images 31-1, 31-2, 31-3, 31-4, 31-5, . . . continuous in the body axis direction.

For example, when the representative pixel value of the image 31-3 in a position "Z" in the body axis direction is calculated, the respective image positions "Z−1" to "Z+1" of the images 31-2 and 31-4 adjacent to the image 31-3 in the body axis direction are set as a search region, and the representative pixel value is calculated. Similarly, e.g., when the representative pixel value in a position "Z−1" in the body axis direction is calculated, image positions "Z−2" to "Z" adjacent in the body axis direction are set as a search region, and the representative pixel value is calculated. With this configuration, it is possible to calculate the representative pixel value of each image without impairing the continuity in the body axis direction.

Further, it may be configured such that processing to discriminate a diagnosis object part from the diagnostic image 31 is added, and the discriminated image region to be a diagnosis object part is set as a search region. As the processing to discriminate a diagnosis object part, a known method such as region growing or pattern matching may be used.

Second Embodiment

The partially emphasized image generation processing according to a second embodiment will be described. The image processing device 100 according to the second embodiment offsets the emphasis effect in the not-diagnosed region 31b to generate the partially emphasized image 39. Note that the configuration of the image processing device 100 according to the second embodiment and the flow of entire processing are the same as those in the first embodiment. Hereinbelow, explanations overlapped with those in the first embodiment will be omitted, but the difference will be described. Further, the respective elements identical to those in the image processing device 100 according to the first embodiment will have the same reference numerals in the description.

Figure 15:
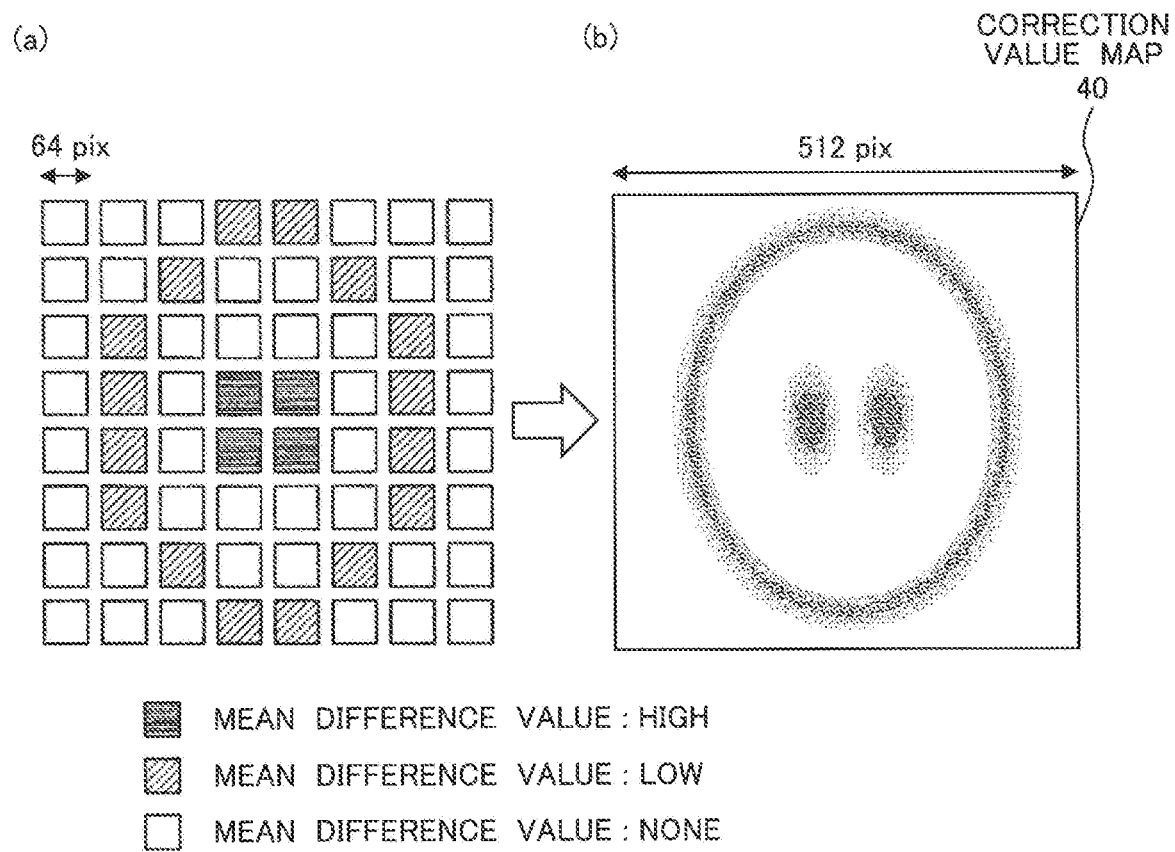
FIG. 15 is a diagram showing an example of generation of a correction value map 40.

As shown in FIG. 15, the CPU 101 first calculates a mean difference value between the diagnostic image 31 and the emphasized image 33 by evaluation block (see FIG. 8). A part where no change occurs before and after the emphasis processing has "no difference". In an evaluation block, the more greatly the difference value is one-sided to positive or negative value, the larger the absolute value of the mean difference value becomes. Accordingly, an evaluation block where the absolute value of the mean difference value of the evaluation block is large is determined as the not-diagnosed part 31b. The calculated difference value is a difference value caused by contrast emphasis processing. Accordingly, it is possible to obtain the partially emphasized image 39 by performing correction of subtracting this value from the not-diagnosed part 31b of the emphasized image 33.

Note that in the above-described correction, with correction by subtraction by evaluation block, as the correction value is changed by evaluation block, the partially emphasized image 39 becomes unnatural. Accordingly, as in the case of the weight map 38 in FIG. 10(b), the correction value by evaluation block is expanded to the pixel size of the diagnostic image, to generate a correction value map 40. The density values of the correction value map 40 represent correction values for the respective pixels.

Figure 16:
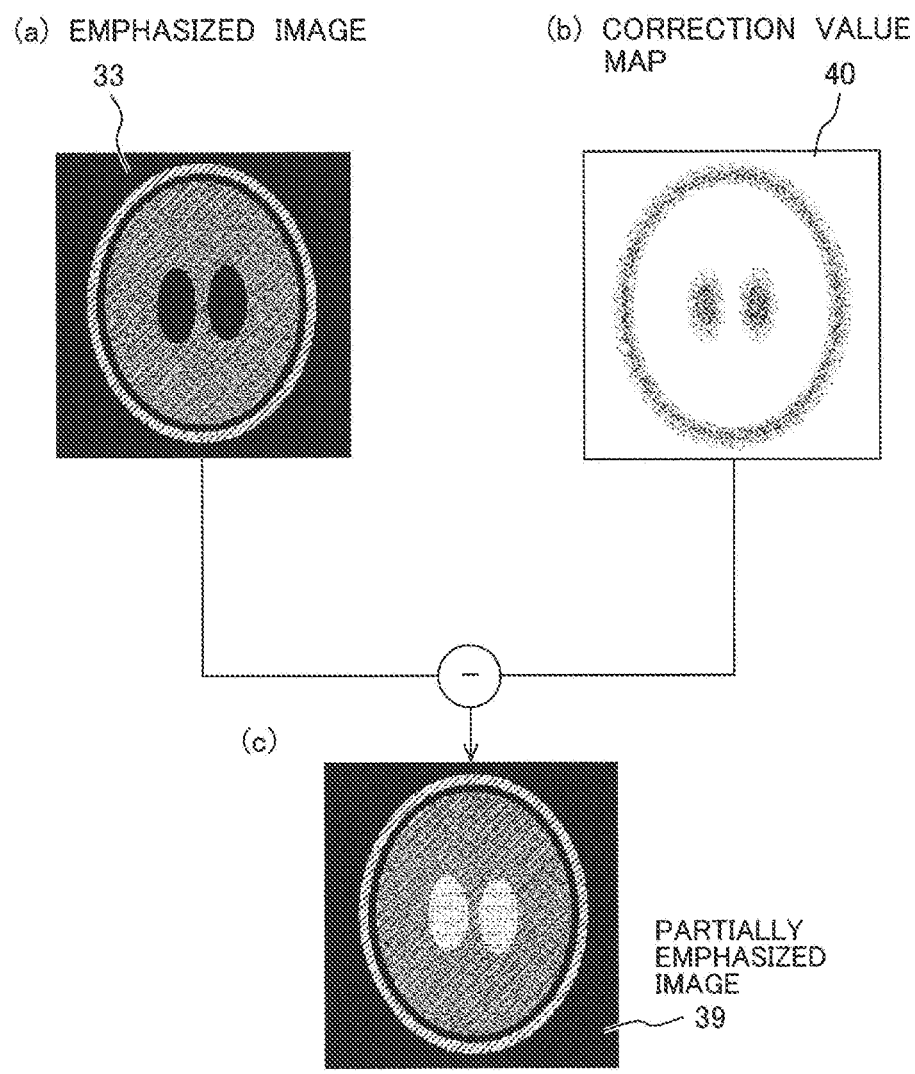
FIG. 16 is a diagram showing an example of calculation of the partially emphasized image 39 using the correction value map 40.

As shown in FIG. 16, the CPU 101 refers to the correction value for each pixel in the correction value map 40, and subtracts it from the pixel value of the corresponding pixel of the emphasized image 33. With this operation, the partially emphasized image 39 is generated.

In this manner, in the image processing device 100, it is possible to generate the partially emphasized image 39 by offsetting the emphasis effect in the not-diagnosed region 33 based on the differential information between the diagnostic image 31 and the emphasized image 33 in each evaluation block. With this configuration, it is possible to perform the procedure of generation of the partially emphasized image 39 in a simple manner.

Third Embodiment

As a third embodiment of the present invention, a display example of the emphasis region and an editing operation of the region will be described. Note that the configuration of the image processing device 100 according to the third embodiment and the flow of entire processing are the same as those in the first embodiment. Hereinbelow, the overlapped explanations will be omitted, and the identical respective elements will have the same reference numerals in the description.

The emphasis region calculated at step S106 is determined based on a parameter previously stored in the storage device 103 of the image processing device 100 or a parameter inputted by the operator. However, the region intended by the operator is not necessarily calculated as the emphasis region. To handle this problem, the image processing device 100 according to the third embodiment provides a user interface for the operator to edit the emphasis region.

Figure 17:
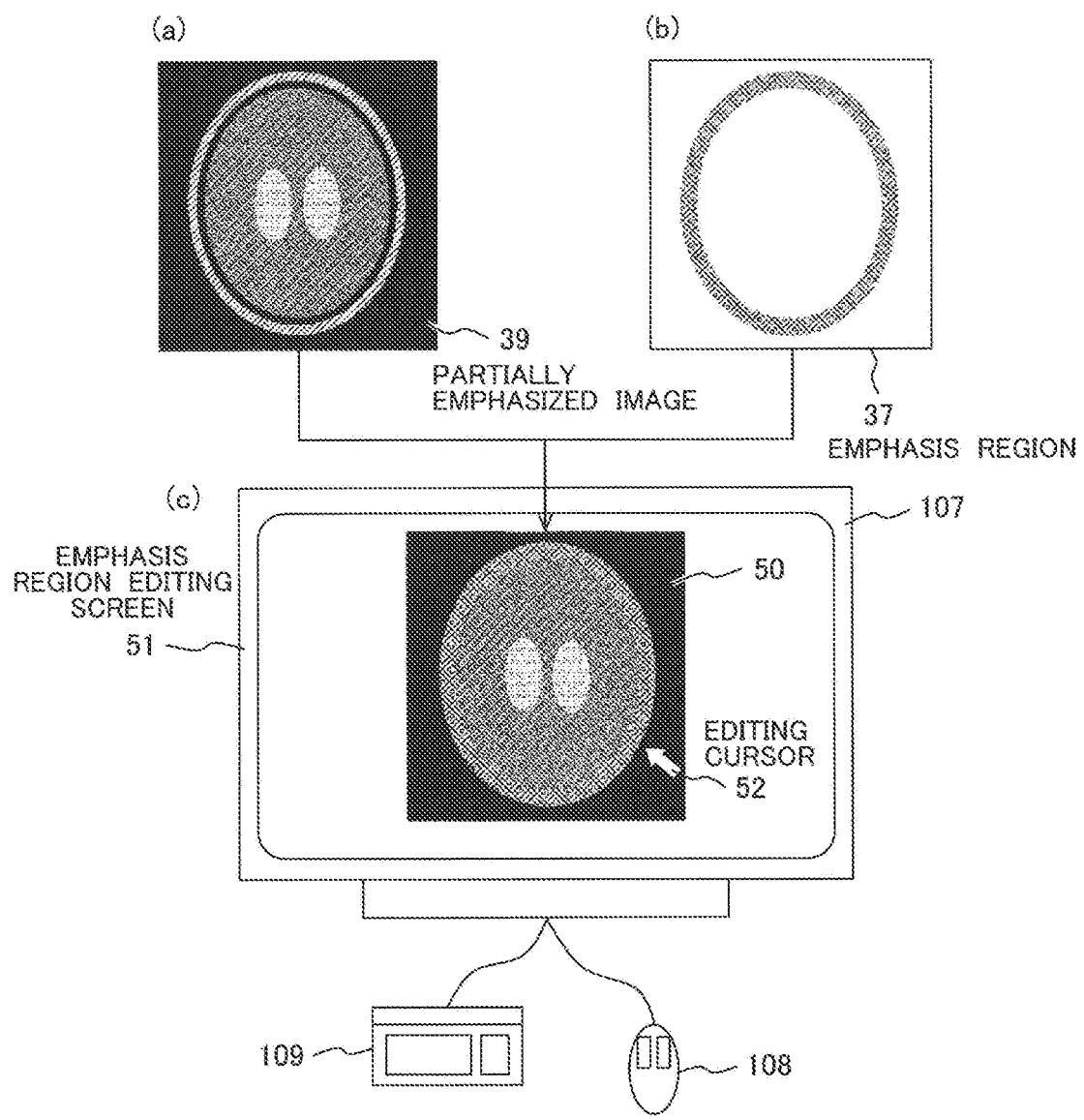
FIG. 17 is a diagram showing an example of an emphasis region editing screen 51.

FIG. 17 shows an example of an emphasis region editing screen 51 as a user interface to edit the emphasis region.

Figure 4:
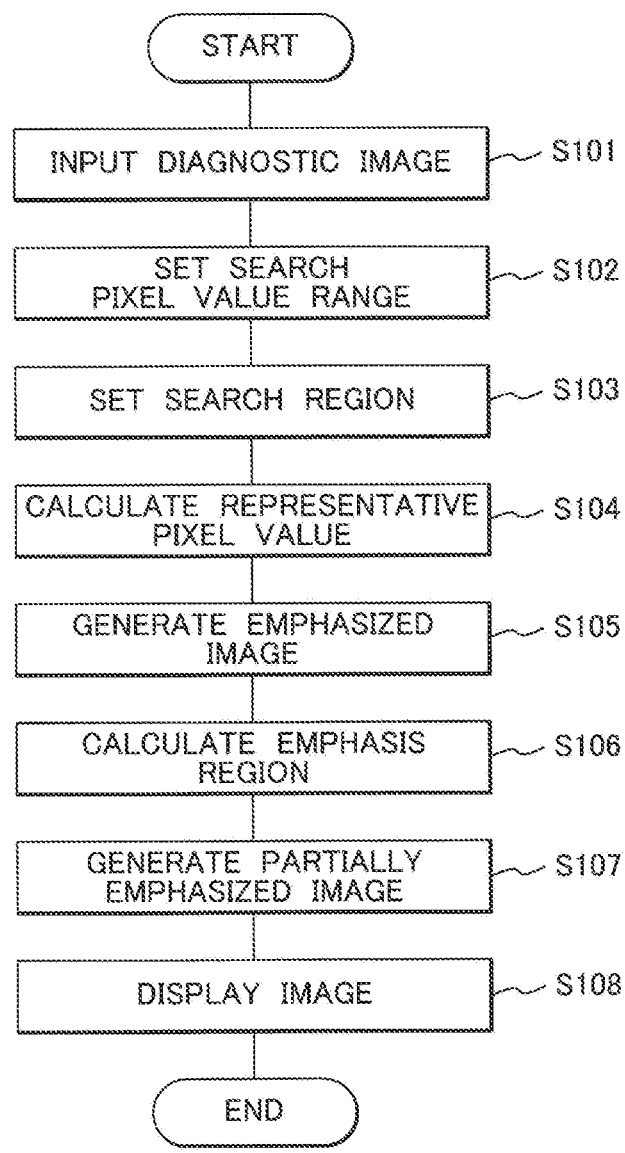
FIG. 4 is a flowchart explaining the flow of partially emphasized image generation processing performed with the image processing device 100.

The CPU 101 displays a superimposed image 50, obtained by superimposing the partially emphasized image 39 generated by the partially emphasized image generation processing according to the first embodiment and an image indicating the emphasis region 37 calculated by the emphasis region calculation processing at step S106 in FIG. 4, on the display device 107. By superimposing the emphasis region 37 on the partially emphasized image 39 and displaying the superimposed image, the operator checks whether or not a desired diagnosed part has been calculated as the emphasis region 37.

Further, the CPU 101 accepts editing of the emphasis region 37 using the mouse 108 and the input device 109 such as a keyboard. That is, by operating the editing cursor 52 using the mouse 108, the input device 109 and the like, an operation to partially delete and/or expand the emphasis region 37 displayed on the display device 107 is accepted. The CPU 101 (partially emphasized image generation unit 27) re-generates the partially emphasized image 39, with the edited emphasis region 37 as input, and re-draws the image on the display device 107.

In this manner, the image processing device 100 according to the third embodiment accepts editing of the emphasis region 37 by the operator, and re-generates the partially emphasized image 39 based on the edited emphasis region 7.

Accordingly, it is possible to generate the partially emphasized image 39 with a region intended by the operator as the emphasis region 37.

Fourth Embodiment

Even in a case where plural diagnosis object parts having different pixel values exist with respect to an inspected part, it is possible to apply the partially emphasized image generation processing according to the present invention. As a fourth embodiment according to the present invention, the partially emphasized image generation processing when plural diagnosis object parts exist will be described. Note that the configuration of the image processing device 100 according to the fourth embodiment and the flow of entire processing are the same as those in the first embodiment. Hereinbelow, the overlapped explanations will be omitted, and the identical respective elements will have the same reference numerals in the description.

For example, regarding a head, as diagnosis objects, white matter, a gray matter border, a bleeding region, an ischaemia region and the like are included. These regions have respectively different pixel values. Accordingly, the image processing device 100 generates one partially emphasized image 57 from plural emphasized images and emphasis regions generated on different conditions.

Figures 18, 19:
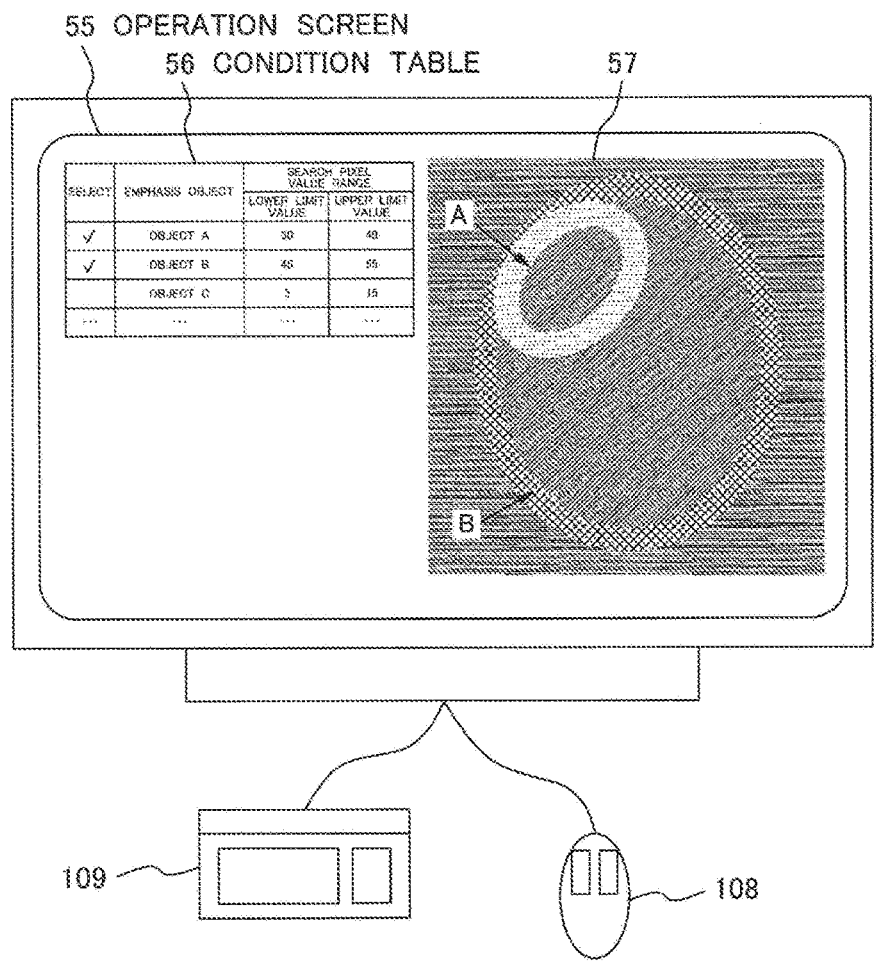
FIG. 18 is a diagram showing an example of an operation screen 55 to generate a partially emphasized image on plural conditions.
FIG. 19 is a diagram showing an example of a condition table 56.

FIG. 18 is a diagram showing an example of an operation screen 55 to generate the partially emphasized image 57 using plural conditions. The CPU 101 displays a condition table 56 to instruct generation of the partially emphasized image and the partially emphasized image 57, on the display device 107.

The operator corrects parameters in the condition table 56 while diagnosing the displayed partially emphasized image 57. The CPU 101 generates a partially emphasized image based on the inputted parameters.

FIG. 19 is a diagram showing an example of the condition table 56.

As shown in FIG. 19, in the condition table 56, the search pixel value range (lower limit value and upper limit value) is defined by part as an emphasis object. Further, a selected mark input column 56a to select a part as an emphasis object is provided. It is possible to select plural parts by designating the selected mark input column 56a with the input device 109, the mouse 108 or the like.

Note that in the operation screen in FIG. 18, parameters of the search pixel value range are editing objects. The degree of emphasis at the emphasized image generation step (step S102), the size of evaluation region referred to at the emphasis region calculation step (step S107) and the like may be used as editing object parameters.

In the example in FIG. 18 and FIG. 19, as emphasis object parts, part A and part B are selected as emphasis objects. The partially emphasized image 57, where the respective parts A and B selected in accordance with the conditions set with the condition table 56 are respectively emphasized, is generated, and is displayed on the display device 107.

Fifth Embodiment

Figure 5:
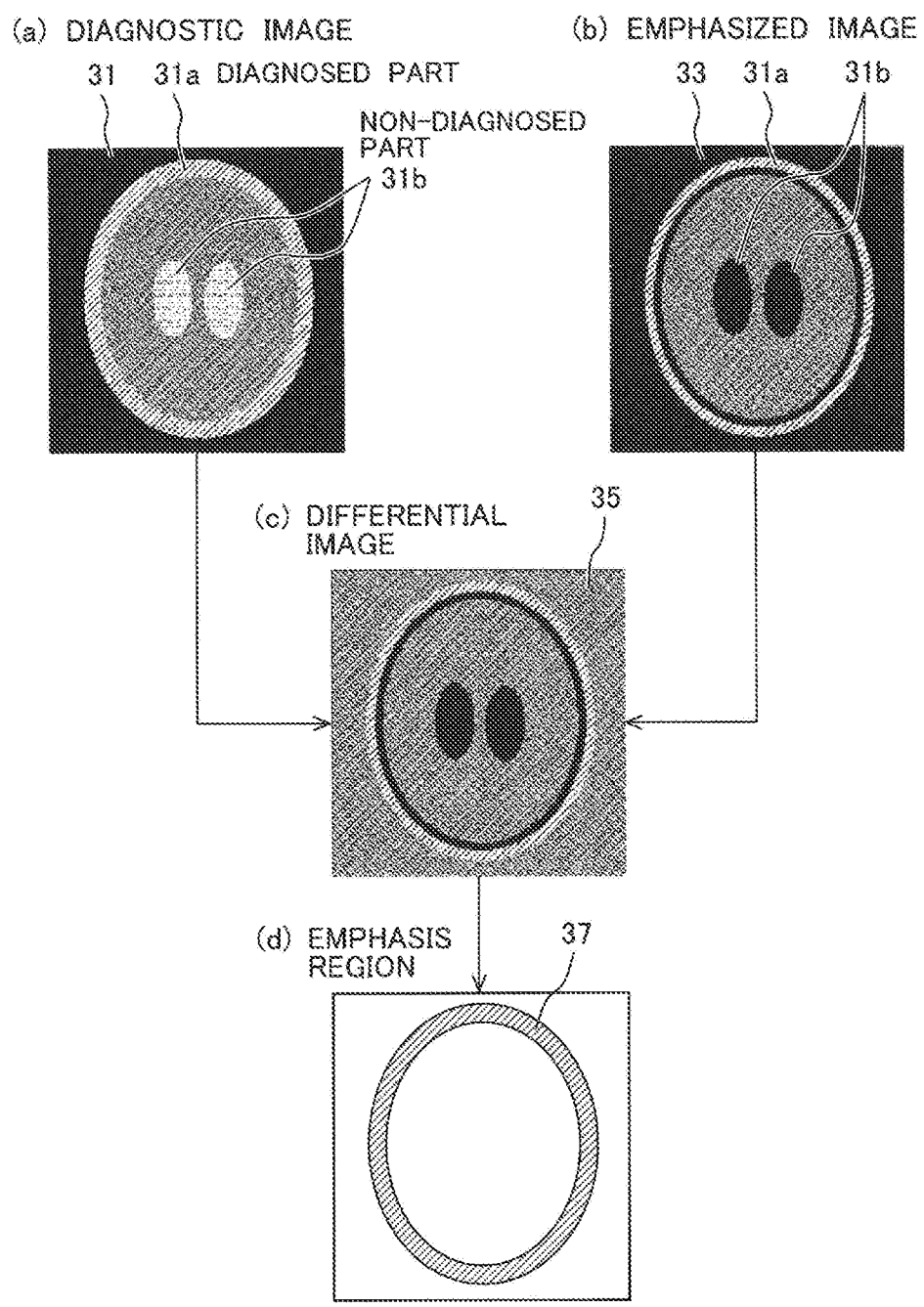
FIG. 5 is a diagram showing an example of a procedure for calculation of an emphasis region 37.
Figure 20:
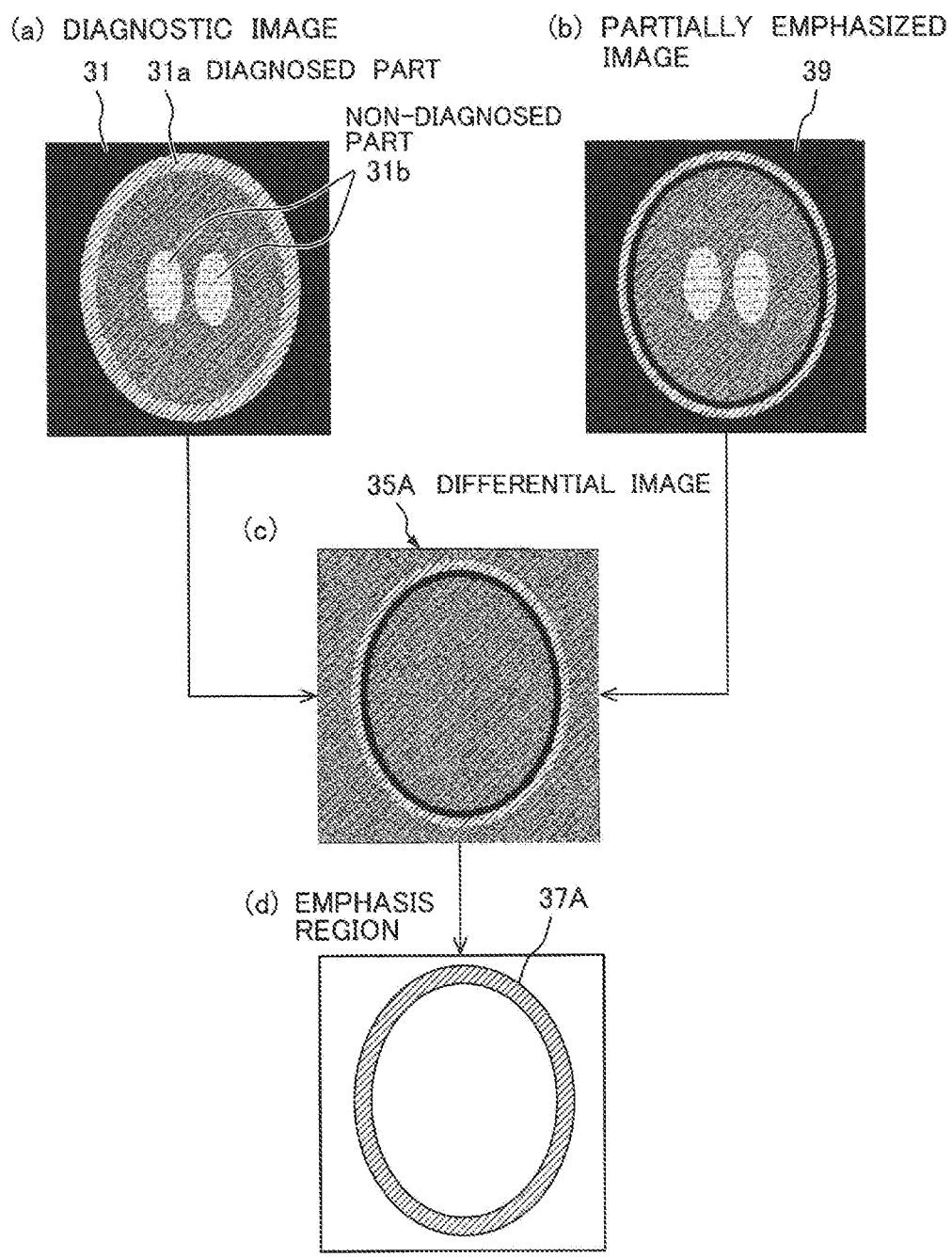
FIG. 20 is a diagram explaining an example of calculation of an emphasis region 37A from differential information between the calculated partially emphasized image 39 and the diagnostic image 31.

In the above-described respective embodiments, the emphasis region 37 is calculated based on the differential information between the diagnostic image 31 and the emphasized image 33 (see FIG. 5 and the like). It may be configured such that the emphasis region 37 in the partially emphasized image 39 is updated to an emphasis region 37A from the differential information between the partially emphasized image 39 and the diagnostic image 31. FIG. 20 shows an example.

As shown in FIG. 20, the CPU 101 (emphasis region calculation unit 26) generates a differential image 35A from the diagnostic image 31 inputted at step S101 in FIG. 3 and the partially emphasized image 39 generated at step S107 in FIG. 3. As in the case of the procedure shown in FIG. 5, when the emphasized image 33 is used as input, differential information remains at a border part of the not-diagnosed part 31b in the differential image 35, in some cases. However, as in the case of the present embodiment, when the input is the partially emphasized image 39, as the differential information from the diagnostic image 31 is not included in a region determined as a region out of the emphasis region, its influence is excluded. Accordingly, the emphasis region 37 is updated, and the emphasis region 37A is accurately calculated.

Further, it is possible to improve the accuracy of emphasis region calculation by repeatedly performing the processing of updating the emphasis region 37A with the diagnostic image 31 and the partially emphasized image 39 as inputs. In this case, the CPU 101 monitors the area and the number of pixels of the emphasis region, and performs control to e.g. terminate the repeated processing when a predetermined condition is satisfied.

As described above, according to the image processing device in the fifth embodiment, the emphasis region 37A is calculated from the differential information between the partially emphasized image 39 and the diagnostic image 31, and the partially emphasized image, where the calculated emphasis region 37A is emphasized, is re-generated. With this configuration, it is possible to accurately calculate the emphasis region 37A.

Sixth Embodiment

Figure 21:
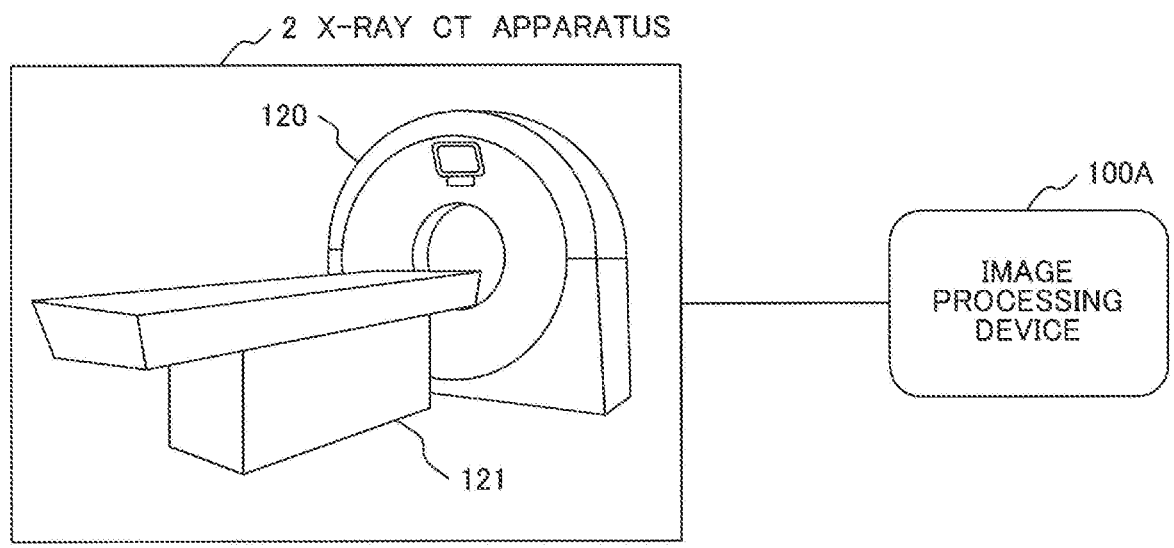
FIG. 21 is a diagram showing an X-ray CT apparatus 2 in which the function of an image processing device according to the present invention is incorporated.
Figure 21:
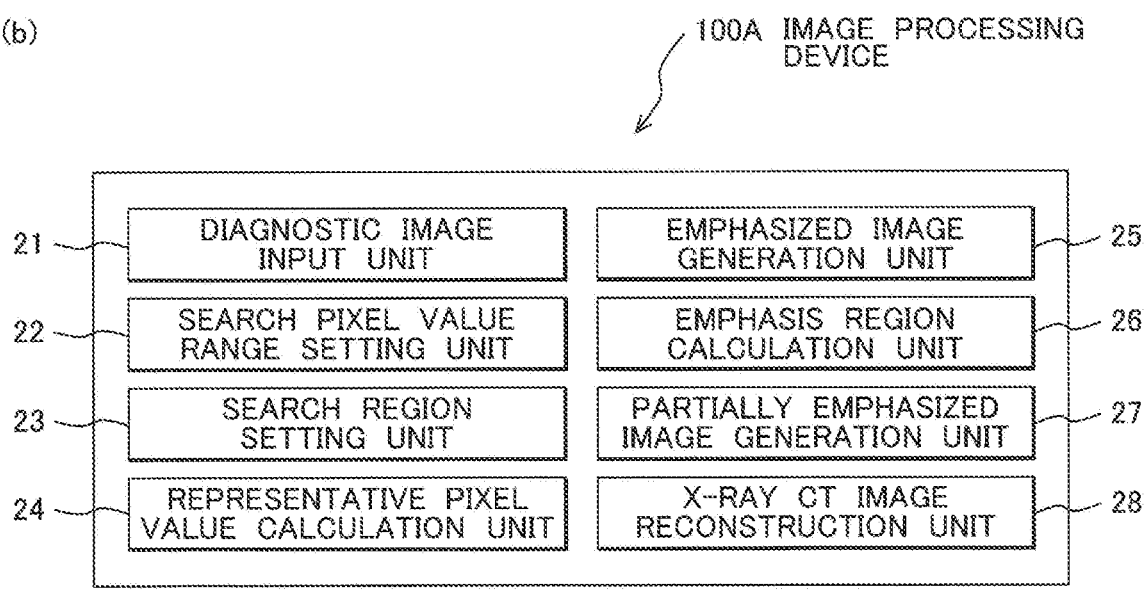

The image processing device 100 shown in the above-described respective embodiments has been explained as a computer or the like to process medical image data as input, as an example. The functions described in the above-described respective embodiments may be incorporated as a part of a medical image diagnosis device. For example, as shown in FIG. 21, the partially emphasized image generation function explained in the above-described respective embodiments may be incorporated in an image processing device 100A for an X-ray CT apparatus 2.

The image processing device 100A has, as functional elements to realize the respective functions explained in the first to fifth embodiment, the diagnostic image input unit 21, the search pixel value range setting unit 22, the search region setting unit 23, the representative pixel value calculation unit 24, the emphasized image generation unit 25, the emphasis region calculation unit 26, the partially emphasized image generation unit 27, and in addition, an X-ray CT image reconstruction unit 28.

The X-ray CT apparatus 2 has a scanner 120 with an X-ray source and an X-ray detector provided in opposite positions on a rotary table, and a bed 121 to insert a subject into an opening of the scanner 120. The scanner 120 irradiates an X-ray to the subject from the respective directions around the subject lying on the bed 121 by rotating the rotary table. The scanner collects X-ray weakening information of the subject from the X-ray transmitted through the subject, and transmits the information to the image processing device 100A.

The X-ray CT image reconstruction unit 28 of the image processing device 100A reconstructs a tomographic image based on the X-ray weakening information of the subject measured with the scanner 120 of the X-ray CT apparatus 2.

The image processing device 100A handles the tomographic image reconstructed with the X-ray CT image reconstruction unit 28 as a diagnostic image inputted into the diagnostic image input unit 21. The image processing device 100A performs the partially emphasized image generation processing explained in the first to fifth embodiments with a CT value of the tomographic image (Hounsfield Unit) as a pixel value.

As described above, preferred embodiments of the image processing device and the like according to the present invention have been explained with reference to the attached drawings. The present invention is not limited to these examples. It is apparent that those skilled in the art could have easily arrived at various modifications or corrected examples within the category of the technical idea disclosed in the present application. It is understood that as a matter of course they also belong to the technical scope of the present invention.

REFERENCE SIGNS LIST

1 . . . image processing system
100, 100A . . . image processing device
101 . . . CPU 101
102 . . . main memory
103 . . . storage device
104 . . . communication I/F
105 . . . display memory
106 . . . I/F
107 . . . display device
108 . . . mouse
109 . . . input device
110 . . . network
111 . . . image database
112 . . . medical image scanning apparatus
120 . . . scanner
121 . . . bed
2 . . . X-ray CT apparatus
21 . . . diagnostic image input unit
22 . . . search pixel value range setting unit
23 . . . search region setting unit
24 . . . representative pixel value calculation unit
25 . . . emphasized image generation unit
26 . . . emphasis region calculation unit
27 . . . partially emphasized image generation unit
28 . . . X-ray CT image reconstruction unit
3 . . . nonlinear grayscale conversion 31 . . . diagnostic image
31a . . . diagnosed part
31b . . . not-diagnosed part
33 . . . emphasized image
35, 35A . . . differential image
37, 37A . . . emphasis region
38 . . . weight map
39 . . . partially emphasized image
40 . . . correction value map
41 . . . search pixel value range data
51 . . . emphasis region editing screen
52 . . . editing cursor
55 . . . operation screen
56 . . . condition table
57 . . . partially emphasized image
A, B . . . object part
P1, P2 . . . specified point

The invention claimed is:

1. An image processing device comprising:
a diagnostic image input that inputs a diagnostic image as image data of a diagnosis object;
a search pixel value range setting computing device that sets a search pixel value range as a pixel value range to search for a representative pixel value on the diagnostic image as reference upon emphasis on contrast of the diagnostic image;
a search region setting computing device that sets a search region as a region to search for the representative pixel value of the diagnostic image on the diagnostic image;
a representative pixel value calculator that calculates the representative pixel value based on the set search pixel value range and the search region;
an emphasized image generator that generates an emphasized image as an image where the contrast of the entire diagnostic image is emphasized with the calculated representative pixel value as reference;
an emphasis region calculator that calculates an emphasis region as a region where the contrast is emphasized from the diagnostic image and the emphasized image; and
a partially emphasized image generator that generates a partially emphasized image as an image where the contrast of the emphasis region is emphasized.

2. The image processing device according to claim 1, wherein the emphasis region calculator obtains a differential value between the diagnostic image and the emphasized image, and calculates the emphasis region based on a magnitude of variation of the differential value.

3. The image processing device according to claim 1, wherein the emphasized image generator generates the emphasized image by performing nonlinear grayscale conversion with the representative pixel value as reference.

4. The image processing device according to claim 1, wherein when the representative pixel value in an arbitrary region stands within a range determined from end values of the search pixel value range, the emphasis region calculator excludes the region from the emphasis region.

5. The image processing device according to claim 1, wherein when the a ratio of pixels within the search pixel value range in an arbitrary region is equal to or higher than a predetermined value, or equal to or lower than the predetermined value, the emphasis region calculator excludes the region from the emphasis region.

6. The image processing device according to claim 1, wherein the emphasis region calculator divides the diagnostic image and the emphasized image into a plurality of evaluation blocks, and by each of the divided evaluation blocks, determines whether or not the block is the emphasis region.

7. The image processing device according to claim 6, further comprising a storage that holds a data set defining a size of the evaluation blocks by inspected part,
wherein the emphasis region calculator determines the size of the evaluation blocks corresponding to the inspected part selected by an operator based on the data set.

8. The image processing device according to claim 6, wherein the emphasis region calculator generates a weight map indicating degrees of emphasis based on the emphasis region determined by evaluation block, and
wherein the partially emphasized image generator generates the partially emphasized image by weight-adding the diagnostic image and the emphasized image based on the weight map.

9. The image processing device according to claim 1, further comprising a storage that holds a data set defining the search pixel value range by the an inspected part,
wherein the search pixel value range setting computing device sets the search pixel value range corresponding to the inspected part selected by an operator.

10. The image processing device according to claim 1, further comprising:
a diagnostic image display that displays the diagnostic image; and
a pixel value acquisitor that acquires a pixel value in an arbitrary position on the displayed diagnostic image,
wherein the search pixel value range setting computing device sets a maximum value and a minimum value of acquired two or more pixel values as the search pixel value range.

11. The image processing device according to claim 1, wherein the search region setting computing device sets a plurality of adjacent images as the search region.

12. The image processing device according to claim 1, wherein the emphasis region calculated with the emphasis region calculator is superimposed on the partially emphasized image generated with the partially emphasized image generator, and the superimposed image is displayed.

13. The image processing device according to claim 2, further comprising an emphasis region editor that edits he a displayed emphasis region, wherein the partially emphasized image generator generates the partially emphasized image based on the an edited emphasis region.

14. The image processing device according to claim 1, wherein the partially emphasized image generator generates the partially emphasized image based on a plurality of emphasized images and emphasis regions generated on different conditions.

15. The image processing device according to claim 1, wherein the emphasis region calculator obtains a differential value between the diagnostic image and the partially emphasized image, and updates the emphasis region based on variation of the differential value in an arbitrary region.

16. The image processing device according to claim 1,
wherein the diagnostic image input inputs a tomographic image generated with an X-ray CT apparatus,
wherein the search pixel value range setting computing device sets a CT value as a search range, and
wherein the representative pixel value calculator calculates the CT value as the representative pixel value.

17. An image processing device comprising:
a diagnostic image input that inputs a diagnostic image as image data of a diagnosis object;

a search pixel value range setting computing device that sets a search pixel value range as a pixel value range to search for a representative pixel value on the diagnostic image as reference upon emphasis on contrast of the diagnostic image;

a search region setting computing device that sets a search region as a region to search for the representative pixel value of the diagnostic image on the diagnostic image;

a representative pixel value calculator that calculates the representative pixel value based on the set search pixel value range and the search region;

an emphasized image generator that generates an emphasized image as an image where the contrast of the entire diagnostic image is emphasized with the calculated representative pixel value as reference;

an emphasis region calculator that calculates an emphasis region as a region where the contrast is emphasized from the diagnostic image and the emphasized image; and a partially emphasized image generator that generates a partially emphasized image as an image where the contrast of the emphasis region is emphasized, wherein the emphasis region calculator divides the diagnostic image and the emphasized image into a plurality of evaluation blocks, and by each of the divided evaluation blocks, determines whether or not the block is the emphasis region, and wherein the emphasis region calculator generates a correction value map from a mean difference value by the evaluation block, and wherein the partially emphasized image generator generates the partially emphasized image by performing correction on the emphasized image by using pixel values of the correction value map.

18. An image processing method using a computer, comprising:

a step of inputting a diagnostic image as image data of a diagnosis object;

a step of setting a search pixel value range as a pixel value range to search for a representative pixel value on the diagnostic image as reference upon emphasis on contrast of the diagnostic image;

a step of setting a search region as a region to search for the representative pixel value of the diagnostic image on the diagnostic image;

a step of calculating the representative pixel value based on the set search pixel value range and the search region;

a step of generating an emphasized image as an image where the contrast of the entire diagnostic image is emphasized with the calculated representative pixel value as reference;

a step of calculating an emphasis region as a region where the contrast is emphasized from the diagnostic image and the emphasized image; and a step of generating a partially emphasized image as an image where the contrast of the emphasis region is emphasized, wherein the emphasis region calculation divides the diagnostic image and the emphasized image into a plurality of evaluation blocks, and by each of the divided evaluation blocks, determines whether or not the block is the emphasis region, and wherein the emphasis region calculation generates a correction value map from a mean difference value by the evaluation block, and wherein the partially emphasized image generation generates the partially emphasized image by performing correction on the emphasized image by using pixel values of the correction value map.

* * * * *